US010288558B2

(12) United States Patent
Das

(10) Patent No.: US 10,288,558 B2
(45) Date of Patent: May 14, 2019

(54) GAS CELL BASED ON HOLLOW-CORE PHOTONIC CRYSTAL FIBER AND ITS APPLICATION FOR THE DETECTION OF GREENHOUSE GAS: NITROUS OXIDE

(71) Applicant: Lakehead University, Thunder Bay (CA)

(72) Inventor: Gautam Das, Thunder Bay (CA)

(73) Assignee: Lakehead University, Thunder Bay (CA)

( * ) Notice: Subject to any disclaimer, the term of this patent is extended or adjusted under 35 U.S.C. 154(b) by 0 days.

(21) Appl. No.: 15/467,361

(22) Filed: Mar. 23, 2017

(65) Prior Publication Data

US 2018/0275048 A1     Sep. 27, 2018

(51) Int. Cl.
| | | |
|---|---|---|
| *G01N 21/3504* | (2014.01) | |
| *G02B 6/02* | (2006.01) | |
| *G01N 21/39* | (2006.01) | |
| *G02B 6/42* | (2006.01) | |
| *G01N 21/359* | (2014.01) | |
| *F16L 15/00* | (2006.01) | |

(52) U.S. Cl.
CPC ......... *G01N 21/3504* (2013.01); *G01N 21/39* (2013.01); *G02B 6/02076* (2013.01); *G02B 6/02328* (2013.01); *G02B 6/4248* (2013.01); *F16L 15/008* (2013.01); *G01N 21/359* (2013.01); *G01N 2021/391* (2013.01); *G01N 2201/088* (2013.01)

(58) Field of Classification Search
CPC ............. G01N 21/3504; G01N 21/359; G01N 2201/088; G02B 6/02328; F16L 15/008
USPC ...................... 356/237.1–237.6, 239.1–239.8
See application file for complete search history.

(56) References Cited

U.S. PATENT DOCUMENTS

| | | | |
|---|---|---|---|
| 8,674,306 B2 * | 3/2014 | Falk ....................... | G01N 21/65 250/343 |
| 2007/0104431 A1 * | 5/2007 | Di Teodoro ....... | G02B 6/02347 385/123 |
| 2016/0327735 A1 * | 11/2016 | Chen .................. | G02B 6/02328 |

* cited by examiner

*Primary Examiner* — Tri T Ton
(74) *Attorney, Agent, or Firm* — Kyle R Satterthwaite; Bryan W Dupuis; Ade & Comapny Inc.

(57) ABSTRACT

Unique gas cell constructions based on a hollow-core photonic crystal fiber are used, for example, inside a fiber ring laser cavity as an intracavity gas cell. In one embodiment, two simple terminal blocks are coupled to opposite ends of the hollow-core photonic crystal fiber. Each block features a main through-bore with an optical window at one end and an optical fiber chuck fitted at the other end, while a transverse bore intersects the main bore and features a gas fitting for connection to a gas source or vacuum pump. In another embodiment, the hollow-core photonic crystal fiber is contained within an enclosure whose exterior walls are fitted with optical windows and gas ports. Inside the enclosure, fiber clamps supports the ends of the hollow-core photonic crystal fiber at positions adjacent to an in alignment with the optical windows.

20 Claims, 8 Drawing Sheets

GAS CELL BASED ON HOLLOW-CORE PHOTONIC CRYSTAL FIBER AND ITS APPLICATION FOR THE DETECTION OF GREENHOUSE GAS: NITROUS OXIDE

BACKGROUND

Trace-gas sensing is a rapidly growing field of research and has received considerable attention, especially in the detection and quantification of greenhouse gases (e.g., $N_2O$ and $CO_2$). It has also applications in non-invasive medical diagnostics, environmental monitoring, and homeland security.

Fertilizers used in agricultural fields are major sources of $N_2O$. The use of fertilizer will increase in the next few decades to meet the demand of food production as the global population increases. However, optimizing the efficiency with which fertilizers produce nutrients, combined with the design of new forms of fertilizers, can reduce their emission of $N_2O$. It is also important to note that the excess fertilizer drains into rivers and lakes due to rain or irrigation and polluting water bodies [1]. Further, the emission of $N_2O$ is spatially variable in soil because of soil factors that lead to the production, consumption, and mobility of the gas. Thus the ability to pin-point "hot spots" of $N_2O$ emissions will allow one to mitigate soil factors. A farmer can regulate the use of fertilizer by measuring the concentration of $N_2O$ emitted from agricultural fields due to the application of fertilizer at different climate and soil conditions. This ability will facilitate the fertilizer industry's worldwide program of 4R (right fertilizer source, right rate, right time and right replacement) Nutrient Stewardship management, which will in turn improve farm management and finally reduce greenhouse gas emissions.

The current widely used technologies (e.g. GC: Gas Chromatograph, FTIR: Fourier Transform Infrared spectroscopy, laser spectroscopy using a lead-salt detector cooled by liquid nitrogen or thermoelectric cooler, and cavity ring down spectroscopy using a quantum cascade laser) to detect trace gases are complex and expensive [2]. Thus, a compact and cost effective system that can operate at room temperature is in demand. A number of important gases (e.g. $CH_4$, $NH_3$, $C_2H_2$, $H_2S$, $N_2O$ and $CO_2$) have overtones of the characteristic absorption (fundamental) and the combinations of the overtones bands in the near-infrared (NIR) region (1-2 μm) of the electromagnetic spectrum, which matches the emission spectrum of rare-earth (e.g. Erbium) doped fiber [3]. This makes it possible to use passive and active optical components available from telecom industries to develop a compact and cost-effective device for the detection of trace gases.

The greenhouse effect is caused by the absorption of infrared radiation (IR) from sunlight by gases such as nitrous oxide ($N_2O$). Qualitatively, gases can be differentiated by their absorption lines, and quantitatively, their concentrations can be determined by measuring the degree of absorption of light directed through a gas sample. The absorption of electromagnetic radiation (e.g. IR or NIR) by a gas is governed by the Beer-Lambert Law [4]:

$$\frac{I}{I_0} = \exp(-\alpha C L) \quad (1)$$

where $I_0$ is the intensity of the incident optical radiation, I is the transmitted optical intensity, a is the absorption coefficient of the gas molecules (an important parameter dependent on both the gas species and the wavelength of incident optical radiation), C is the concentration of the absorbing molecules and L is the optical path length of the gas cell or absorption path length. In general, absorption spectroscopy (e.g. FTIR) makes use of incoherent light sources such as incandescent bulbs to generate IR radiation. These sources are essentially blackbody radiators, and complex optical components are required to collimate and direct the beam through the sample with narrow bandwidth. The sensitivity of the above devices is limited by the physical length of the gas cell. Highly sensitive spectroscopic techniques to enhance the absorption path length have been developed based on the laser, such as continuous-wave cavity ring-down spectroscopy (CW-CRDS) and intracavity laser absorption spectroscopy (ICLAS) [5]. The conventional CRDS technique involves measuring the decay time of the laser pulse injected into a high finesse cavity (Fabry-Perot or Ring configuration) that contains the gas sample, where the rate of decay of the pulse indicates the absorption by the gas sample. One can calculate the concentration of the gas sample from the decay time or the ring-down time. On the other hand, in ICLAS, the gas cell is used inside the laser cavity and no external laser is required. Both CRDS and ICLAS increase the effective absorption length by several times, compared to conventional FTIR systems [5]. As the path length is enhanced, the sensitivity of the device increases. Thus, combining advanced detection techniques with a gas cell with longer optical path length makes it possible to develop a very highly sensitive gas detection system.

In the present Application, details are provided concerning the design of novel gas cells, and their application for the detection of greenhouse gas; more specifically, nitrous oxide ($N_2O$).

SUMMARY OF THE INVENTION

According to a first aspect of the invention, there is provided a gas absorption cell apparatus comprising at least one terminal block for coupling to a first end of a hollow core photonic crystal fiber to cooperate with a like terminal block at an opposing second end of the hollow core photonic crystal fiber to form a fiber-based gas absorption cell, wherein each terminal block comprises:

a solid block of air-impermeable material having a main through-bore extending fully through the block from an optical-coupling end of said block and opposing fiber-coupling end of said block;

an optical window fitted in the main through-bore at the optical-coupling end of said block to enable admission or exit of light energy to or from said main through-bore;

an optical fiber chuck fitted in the main through-bore at the fiber-coupling end of said block to receive a respective end of the hollow core photonic crystal fiber and position said end within the main through-bore in alignment behind said optical window for optical communication therewith;

a transverse bore extending into said block from a gas-coupling side thereof and intersecting with said main through-bore at an intermediate location between said ends of the block to enable admission or evacuation of gas to or from the end of the hollow core photonic crystal fiber via said transverse bore.

Preferably there is internal threading within the transverse bore for receiving a threaded gas fitting at the gas-coupling side of the block end for said admission or evacuation of said gas via said fitting.

Preferably the main through-bore, at the optical-coupling end thereof, comprises a counter-bored area of enlarged diameter in which the optical window is mounted.

Preferably there is a threaded connection between the fiber chuck and the block, whereby the fiber chuck is readily removable from the block for selective disconnection of the respective end of the hollow core photonic crystal fiber.

Preferably there is external threading carried on the fiber chuck and internal threads provided in the main through-bore adjacent the fiber-coupling end of the block, the fiber chuck being fitted with the main through-bore by engagement of the external threading on the fiber chuck with the internal threads of the main through-bore.

Preferably the external threading carried on the fiber chuck is defined by an externally threaded carrier through which the fiber chuck axially extends.

Preferably the externally threaded-carrier comprises an externally threaded shaft and an enlarged head of greater diameter than said threaded shaft by which rotation of the externally threaded carrier can be driven to engage and disengage said externally threaded carrier from the internal threading of the main through-bore.

Preferably there is an o-ring seal circumferentially disposed around the fiber chuck and clamped between an end of the externally threaded carried carrier and an inwardly reaching shoulder of the block at a transition between a counter-bored section thereof at which the internal threads are defined and an adjacent reduced-diameter section of the main-through bore.

Preferably the fiber chuck has an externally threaded end disposed outside the block, a cap with a threaded axial bore extending thereinto from a first end of the cap is engaged to the externally threaded end of the fiber chuck via mating of said threaded axial bore with the threaded end of the fiber chuck, a seal is axially compressed between an end of the axial bore and the threaded end of the fiber chuck and is circumferentially tightened around the fiber, which passes through the threaded bore of the cap via a smaller axial bore that communicates therewith.

Preferably the externally threaded end of the fiber chuck is situated past the externally threaded carrier.

Preferably there are two terminal blocks for respectively coupling to the first and second ends of the hollow core photonic crystal fiber.

Preferably said two terminal blocks are identical.

According to a second aspect of the invention, there is provided a method of producing a terminal block for a gas absorption cell apparatus employing two such units attached to opposing ends of a hollow core photonic crystal fiber, said method comprising obtaining a solid block of air-impermeable material, boring a main through-bore through said block from a first end thereof to an opposing second end, boring a transverse bore into said block from one side thereof to a point intersecting said main through-bore at an intermediate location between said first and second ends of the block, mounting an optical window in the main through-bore at the first end of the block, and providing a releasable connection to the main through-bore at the second end of the block for removable mounting of a fiber chuck in the main through-bore in order to hold a respective end of the hollow core photonic crystal fiber within the main through-bore at a position behind the optical window and in fluid communication with the transverse bore to enable optical communication between said optical window and said end of the hollow core photonic crystal fiber and admission or evacuation of gas to or from the hollow core photonic crystal fiber via said transverse bore.

Preferably the method includes counter-boring the main through-bore at the first end of the block to form an area of enlarged diameter for mounting of the optical window.

Preferably the method includes introducing a flowable sealant into said area of enlarged diameter during installation of the optical window therein to create an air-tight seal between the optical window and the main through-bore that prevents escape of gas from the main through-bore at the first end of the block.

Preferably the method includes boring the main through-bore with multiple diameters, including boring a reduced diameter section of the main through-bore at an intermediate location between the second end of the block and the location at which the transverse bore intersects the main through-bore, and boring a larger counter-bored section of the main through-bore at the second end of the block so that a transition between the reduced diameter section and the larger counter-bored section defines an inwardly reaching shoulder for receiving an o-ring that is compressed against said shoulder by threaded coupling of the fiber chuck to the block at the second end thereof.

Preferably the method includes coupling the fiber chuck to the block in a position placing an externally threaded end of the chuck outside the block and supporting the hollow core photonic crystal fiber in a position passing axially through said chuck, threading a removable cap, through which the hollow core photonic crystal fiber passes, onto the externally threaded end of the fiber chuck, and advancing said cap into a tightened position axially compressing a seal against the threaded end of the fiber chuck and circumferentially tightening said seal around the hollow core photonic crystal fiber.

According to a third aspect of the invention, there is provided a method of adjusting the effective length of a gas absorption cell apparatus comprising an initial hollow core photonic crystal fiber running between two terminal blocks respectively coupled to opposing ends of said initial hollow core photonic crystal fiber in a manner holding said respective ends in respective chambers of the terminal blocks to and from which gas is admissible and evacuatable via respective gas fittings of said terminal blocks, the method comprising decoupling said opposing ends of said initial hollow core photonic crystal fiber from said terminal blocks, and substituting a replacement hollow core photonic crystal fiber of different length by respectively coupling opposing ends of the replacement hollow core photonic crystal fiber to said terminal blocks in place of the initial hollow core photonic crystal fiber.

According to a fourth aspect of the invention, there is provided a hollow core photonic crystal fiber gas absorption cell apparatus comprising a singular enclosure delimiting an interior space that is closed or closable in an air-tight manner sealed off from a surrounding exterior environment, optical input and output windows both optically communicating the interior space of the enclosure with a surrounding exterior environment, a first fiber support mounted within the interior space of the enclosure proximate the optical input window to support a first end of a hollow core photonic crystal fiber proximate said optical input window to accept incoming light energy admitted to the interior space of the enclosure via said optical input window, a second fiber support mounted within the interior space of the enclosure proximate the optical output window to support a second end of the hollow core photonic crystal fiber proximate said optical output window to release light energy from said hollow core photonic crystal fiber to the exterior environment via said optical output window, a gas inlet communicating with the interior space and connected or connectable to a supply of gas to admit gas into said interior space, and a gas outlet for evacuating said gas from said interior space, whereby said gas admitted into said interior space is admissible and evacuatable to and from the hollow core photonic crystal fiber via the ends of said hollow core photonic crystal fiber positioned inside said interior space by said fiber supports.

According to a fifth aspect of the invention, there is provided a hollow core photonic crystal fiber gas absorption cell apparatus comprising a singular enclosure delimiting an interior space that is closed or closable in an air-tight manner sealed off from a surrounding exterior environment, optical input and output windows both optically communicating the interior space of the enclosure with a surrounding exterior environment, a hollow core photonic crystal fiber situated within the interior space of the enclosure with a first end of a hollow core photonic crystal fiber situated proximate said optical input window to accept incoming light energy admitted to the interior space of the enclosure via said optical input window, and a second end of the hollow core photonic crystal fiber situated proximate said optical output window to release outgoing light energy from said the hollow core photonic crystal fiber to the exterior environment via said optical output window, a gas inlet communicating with the interior space and connected or connectable to a supply of gas to admit gas into said interior space, and a gas outlet for evacuating said gas from said interior space, whereby said gas admitted into said interior space is admissible and evacuatable to and from the hollow core photonic crystal fiber via the ends of said hollow core photonic crystal fiber positioned inside said interior space.

A surface of the hollow core photonic crystal fiber may be provided with holes at intermediate locations between the ends of the hollow core photonic crystal fiber.

Preferably a floor of the enclosure is equipped with an optical breadboard.

Preferably the enclosure is selectively openable and closeable to enable removable and replacement of said hollow core photonic crystal fiber.

BRIEF DESCRIPTION OF THE DRAWINGS

One embodiment of the invention will now be described in conjunction with the accompanying drawings in which:

FIG. 10A shows absorption spectrum of 10% N2O from the FIG. 4 experimental setup after subtracting the N2 gas spectrum as background for a 20 meter length of PCF in the first embodiment gas cell.

In the drawings like characters of reference indicate corresponding parts in the different figures.

DETAILED DESCRIPTION

Figure 1A:
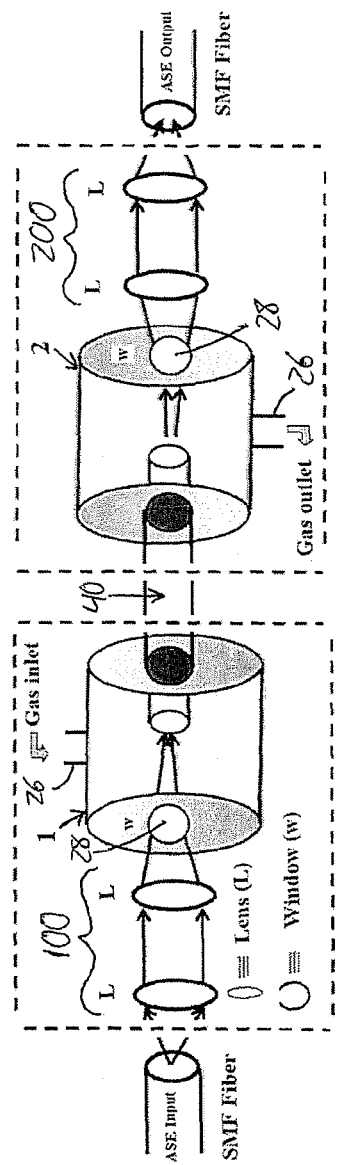
FIG. 1A is a schematic illustration a first embodiment gas cell based on a hollow-core photonic crystal fiber (PCF), where each end of the hollow-core PCF is physically supported in an internal chamber of a terminal block through which gas is admissible and evacuable.
Figure 1B:
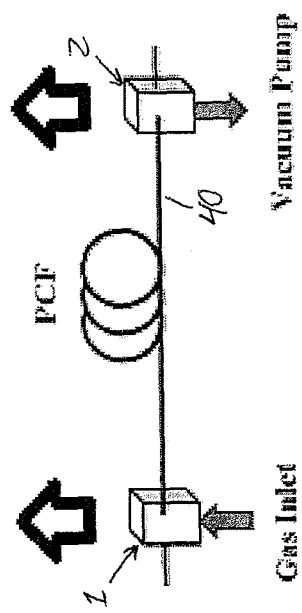
FIG. 1B is a more simplified schematic illustration of the first embodiment.
Figure 1C:
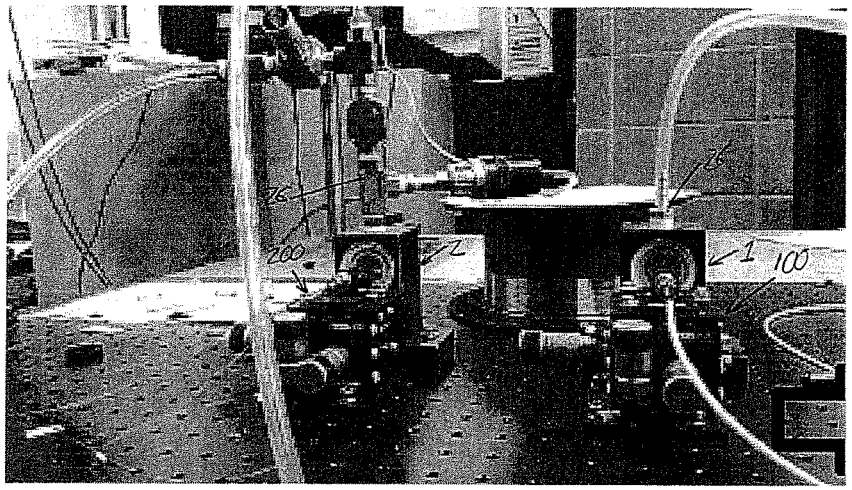
FIG. 1C is a photographic image of a prototype gas cell according to the first embodiment, where a spool of hollow-core PCF has each of its ends physically coupled to the respective terminal blocks, which in turn are optically coupled to respective lens assemblies.

In development of the present invention, a hollow-core photonic crystal fiber (PCF) was used to design a gas cell, and was incorporated as an intracavity gas cell in a fiber ring laser. The detailed structure of the laser cavity was described in reference [6]. The amplified spontaneous emission (ASE) light inside the laser cavity was used for the detection. In general, an erbium doped fiber gives a very wide (~100 nm) ASE spectrum. A fiber Bragg grating (FBG) with peak wavelength close to one of the absorption lines was chosen and the system produced the laser at this wavelength. The wavelength was close to the lower side of the emission spectrum, where the absorption coefficient of $N_2O$ is higher, compared to that in the C and L band regions. $N_2O$ gas has three fundamental infrared active absorption bands: $u_1$=1284.9 cm-1~7.8 μm; $u_2$=588.8 cm-1~17 μm; and $u_3$=2223.8 cm-1~4.5 µm. A number of articles, reporting results from different spectroscopic techniques such as Fourier Transform Infrared Absorption Spectroscopy (FTIR), Intracavity Laser Absorption Spectroscopy (ICLAS), and Cavity Ring Down Spectroscopy (CRDS), identify transitions in the overtone bands for $N_2O$ gas [7-19].

In the experimental system detailed herein, the rotational line in the $3u_3$ overtone band (~1.52 µm band) available from HITRAN was used as a reference line to develop the sensing device [20]. The system based on the new gas cell was capable of detecting $N_2O$ at a concentrations level of sub-ppmv (parts per million by volume). The efficiency of the device has been explored using different lengths of hollow-core photonic crystal fiber (PCF) and spectroscopic techniques. The system based on the developed gas cell will be compact and cost-effective compared to the system based on conventional gas, which have larger foot print.

A gas cell that requires a very small amount (~ml) of gas is important for high sensitivity laser absorption spectroscopy. In this respect, a hollow-core photonic crystal fiber (PCF) is a good candidate because of the high optical-path-to-sample-volume ratio [21-23]. In a PCF, light propagates through the hollow core by photonic band gap effects, which occur due to the periodic distribution of air holes in the cladding [24]. The PCF is very attractive for applications in optical communications, because it shows very low attenuation, dispersion, non-linearity, bending loss, and can also guide a fundamental mode over a wide spectral range without any leakage [25,26]. The idea of using a PCF for gas and liquid sensing is relatively new and there is scope to develop a new compact device using this fiber [27-29]. An all-fiber gas cell has been proposed and demonstrated for gas detection [30]. Recently a number articles have been published on gas sensors based on PCF in CRD spectroscopy [31,32], wavelength modulation spectroscopy (WMS) [33], ICAS [34] and Raman spectroscopy [35]. Most of the gas cells developed using a PCF are designed to detect a particular chemical or gas [31,36-39]. In references [40-43], the dynamics of gas flow in PCF, which determine the filling and evacuation time for the PCF-based gas cell, have been investigated. In order to reduce the filling and evacuation time and thus increase the response time of the detection system, researchers used a number of techniques, such as splicing the PCF to a normal single-mode fiber and allowing the gas sample to fill the core at a higher pressure [28], drilling holes on the surface of PCF so that gas can diffuse faster [44-46], using specially designed mechanical splices [47,48] and finally using a specially designed fiber [49]. It is important to note that the commercially available gas cell based on PCF from GLO photonics (UK) does not allow one to change the fiber if required.

FIG. 1 shows the prototype gas cell developed by the present inventors using a hollow-core photonic crystal fiber [HC19-1550, core diameter: 20 µm] from NKT Photonics to detect trace gases. The system has two lens system assemblies 100, 200, together with two solid terminal blocks 1, 2, for example whose outer dimensions may be 2"×2"×4", and which may be made of aluminum, steel, other metals, or other gas-impermeable solids. A very small hole was drilled inside each block, so that the volume of the gas admissible inside was very small—only a few ml. One terminal block 1, 2 is coupled to one end the hollow-core PCF 40 and is connected to a gas supply 32, and the other terminal block is coupled to the other end of the hollow-core PCF 40 and is connected to a vacuum pump 29. The illustrated embodiment uses the same identical design for both terminal blocks 1, 2, so that each be connected to either a gas supply or a vacuum pump. During experimental use of the prototype, the hollow-core fiber 40 was evacuated using the pump 29, and the vacuum level was maintained at approximately 0.2 mb, when evacuated from one side only. It was important to adjust the optimum pressure difference between the two terminal blocks 1, 2 for a steady gas flow through the hollow-core PCF 40 from the supply 32. The time to evacuate a 20 meter long PCF was approximately 80 minutes, which led to a slow response time for the system. The experiment was repeated with a 40 meter length of PCF. The increased fiber length caused a longer gas evacuation and filling time. To improve the filling time, the gas was allowed to diffuse from one end while other side was connected to the vacuum pump, and, after some time, gas was allowed to diffuse from both ends.

Figure 1D:
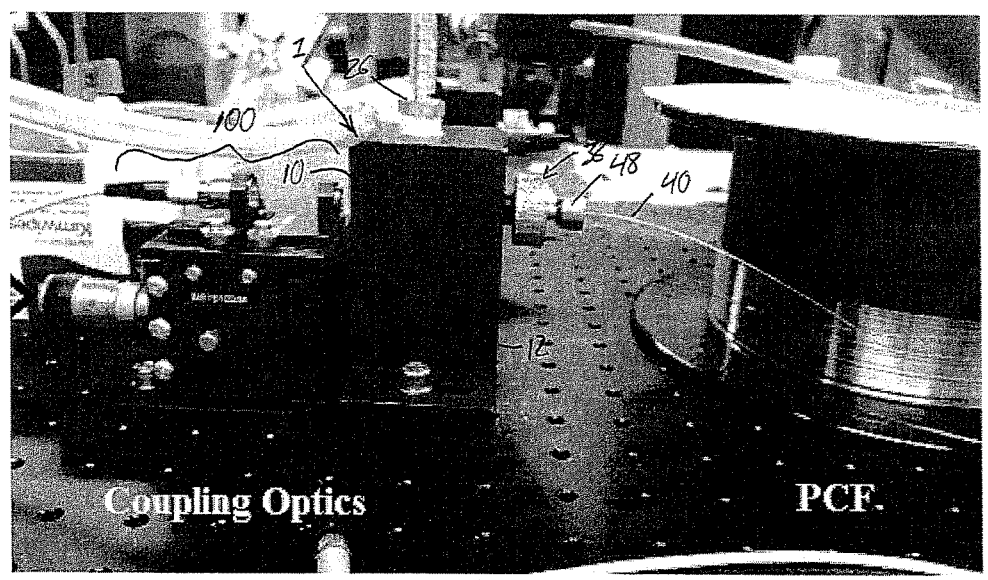
FIG. 1D is another photographic image of the first embodiment prototype from another viewing angle.

The front end of each block was fitted with an AR (antireflection) coated quartz window 28 for coupling of light to or from the respective lens assembly, and the opposing rear end was fitted with fiber coupling components. Accordingly, the front and rear ends are also referred to herein as the optical coupling and fiber coupling ends, respectively. The top of block 2 was fitted with a gas on/off switch or control valve 31, and a vacuum gauge 30. To eliminate leakage through the fiber chuck 38 at the rear end of the block, a specially designed O-ring and cap assembly 46, 48 was used as part of a unique fiber connector. FIG. 1D shows how the PCF was inserted inside the aluminum block using the custom-designed connector. The advantage of this system was that it could maintain a constant vacuum level (e.g. ~0.2 mb) at one end of the fiber while allowing gas to diffuse through the other end. During the filling process, the fiber was evacuated from both sides of the PCF for a certain amount of time, and then one end of the PCF was maintained at a lower pressure and the other end was connected to a gas supply in the form of a Tedlar bag filled with $N_2O$ gas at a particular concentration. [Two gas tanks, one with $N_2O$ and other with $N_2$ from Praxair, Canada, and a mass flow controller from Omega, was used to prepare specific mixtures of gas. Both tanks were connected directly to 100 nm filters in order to remove any dust particles contained in the gas]. The optical fiber at the input (and output) and lenses in each assembly were mounted on a three-axis stage. As shown in FIG. 1A, one lens collimated the beam and the other one focused the collimated beam on the tip of the PCF through the quartz window.

Figure 2:
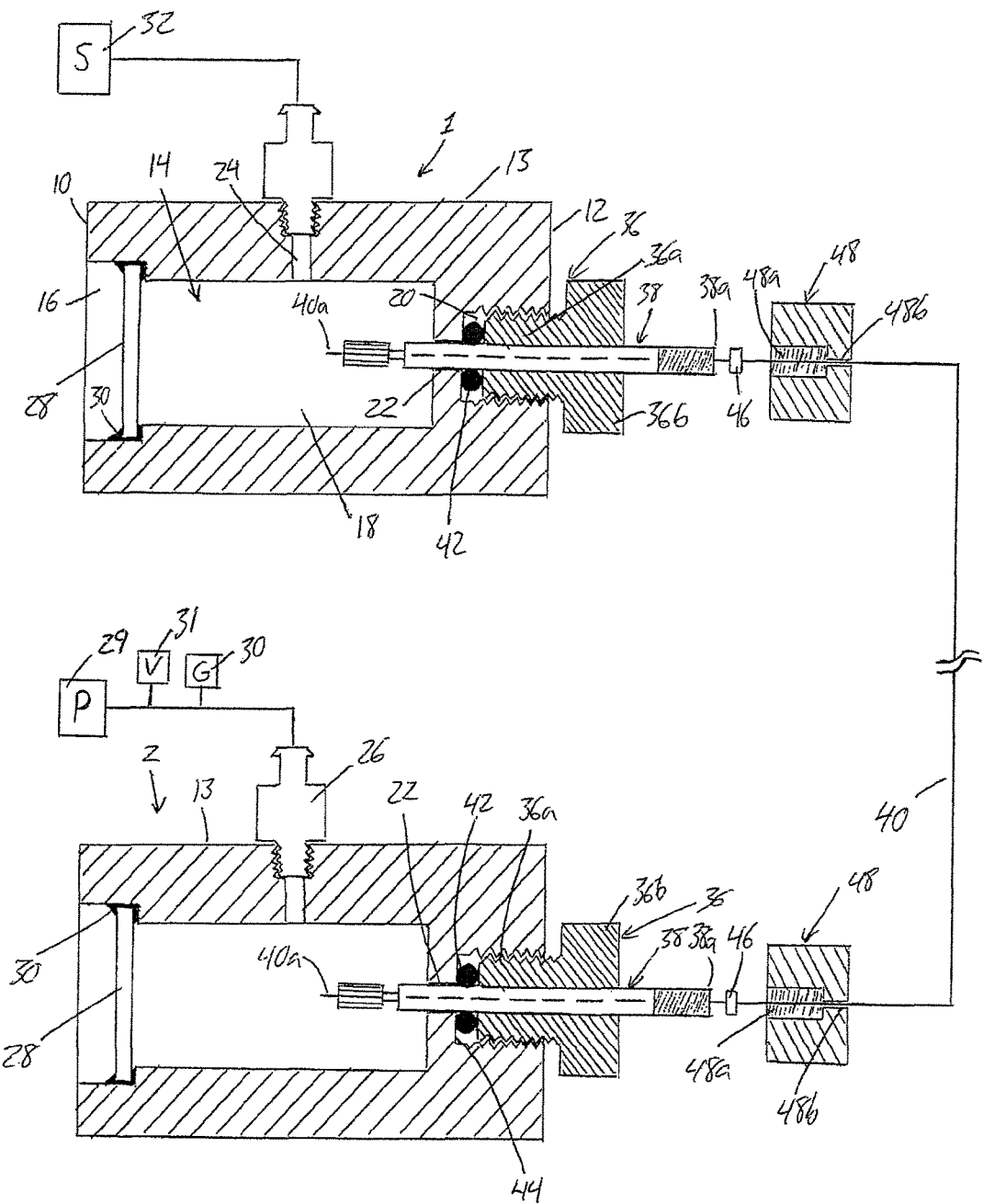
FIG. 2 is a schematic cross-sectional view of the terminal blocks of the first embodiment.

FIG. 2 reveals further structural detail of the terminal blocks 1, 2 and the coupling of the hollow core PCF 40 thereto. Each block has a front optical coupling end 10 and an opposing rear end 12. A main through-bore 14 is drilled longitudinally through the block from the front end thereof to the opposing rear end, but is drilled in multiple sections of varying diameter. A counter-bored section 16 of greatest diameter resides at the front end of the block, and opens into a gas receiving section 18 of lesser diameter. A smaller counter-bored section 20 at the rear end of the block is threaded, and is joined to the gas receiving section 18 by a reduced or constricted section 22 of lesser diameter than the other sections. A transverse bore 24 is drilled into the block from one side thereof, for example the top side 13 in the illustrated example, and terminates where it intersects with the gas receiving section 18 of the main through-bore 14. The transverse bore 24 is internally threaded where it intersects with the side wall 13 of the block, and the smaller counter-bored section 20 at the rear end 12 of to block is likewise internally threaded. A gas fitting 26 is threaded into the transverse bore 24 of each block 1, 2 in air-tight relation therewith, for example using thread tape to ensure an air-tight seal. The gas fitting 26 of block 2 is connected to a vacuum pump 29, vacuum gauge 30 and control valve 31, and the gas fitting 26 of block 1 is connected to a gas supply 32.

The quartz window 28 is seated within the large counter-bored section 16 at the front end 10 of the block. Before and/or after the insertion of the quartz window 28 during production of the block, a flowable sealant is applied around the peripheral wall of this section so as to form an air-tight seal 30 between the window 28 and the wall of the main through-bore, thus preventing escape of gas from the neighbouring gas receiving section 14 through the front end 10 of the block.

At the rear end 12 of each block, an axially-bored bolt 36 has its externally threaded shaft 36a engaged with the internal threading of the rear counter-bored section 20, while the larger diameter head 36b of the bolt 36 resides outside the block beyond the rear end 12 thereof. The bolt 36 has a central though-bore passing axially therethrough from the head to the distal end of the threaded shaft. The fiber chuck 38 is received within this through-bore, and extends axially from each end of the bolt 36. The bolt thus serves as a carrier of the fiber chuck 38, and the bolt shaft 36a defines an external set of threads spanning a partial length of the chuck's elongated body in order to mate with the rear threaded section 20 of the block's main through-bore 14. The enlarged head 36b of the bolt remains outside the block for manual or tool-driven rotation of the bolt during installation and removal thereof to and from the block. While the bolt 36 may have a hexagonal head for wrench-driven operation thereof, the prototype in the drawings instead features a round head, but with a knurled or otherwise textured outer peripheral surface for manually gripped turning of the bolt.

The fiber chuck 38 reaches through the reduced diameter section 22 of the block's main through-bore into the gas-receiving section 18 thereof, where a free end 40a of the hollow-core PCF 40 emerges from the fiber chuck 38 on the central axis of the block's main through bore. Accordingly, gas introduced or evacuated to or from the gas-receiving section of the block's main through-bore 14 via the transverse bore 24 can enter or exit the hollow-core PCF 40 through the free end 40a thereof. So that the gas-receiving section 18 of the block's main through bore defines an air-tight gas chamber, an o-ring seal 42 is situated around the fiber chuck 38 between the distal end of the carrier bolt's threaded shaft 36a and the inwardly reaching shoulder 44 defined at the transition between the rear counterbored section 20 of the block's main through-bore and the adjacent reduced-diameter section 22 thereof. The o-ring 42 is axially compressed against the inwardly reaching shoulder of the block by the distal end of the bolt 36 when tightened, whereby the o-ring 42 circumferentially tightens around the fiber chuck 38. This cooperates with the sealant-retained position of the quartz window 28 and the air-tight threaded engagement of the gas fitting 26 with the block to maintain an air-tight status of the gas receiving section of the block's main through-bore. Accordingly, gas can only enter and exit the block through the gas fitting 26 and the fiber chuck 38.

To similarly provide an air-tight seal between the hollow-core PCF 40 and the fiber chuck 38, the hollow-core PCF 40 passes through a smaller o-ring seal 46 just outside a threaded exterior end 38a of the chuck 38, and an internally threaded cap 48 is threaded onto the chuck 38 in order to axially compress the smaller o-ring seal 46 against the threaded end of the chuck, and thus circumferentially constrict the smaller o-ring seal 46 around the hollow-core PCF 38. FIG. 2 shows the cap 48 and corresponding seal 46 in exploded positions prior to threading of the cap onto the fiber chuck. The cap's threaded axial bore 48a extends into the block-facing inner end of the cap 48, but stops short of the opposing outer end of the cap 48. A smaller axial bore 48b of the cap continues onward from the threaded bore 48a to the outer end of the cap, and accommodates passage of the hollow-core PCF fully through the cap 48, and onward through the chuck 38 and into the block. When the cap 48 is sufficiently threaded onto the chuck 38, the seal 46 is axially compressed between the chuck's threaded end and the closed end of the cap's threaded bore, which causes the seal 46 to tighten around the hollow-core PCF 40. This maintains the air-tight state of the block's gas-receiving section 18 by sealing closed the annular space between the fiber 40 and the chuck 38 at the threaded outer end 38a thereof. Accordingly, gas can only enter and leave the block via the hollow-core PCF 40 and the gas fitting 26.

The forgoing terminal block design is easily manufactured, requiring only a singular block of stock material and basic drilling and tapping machinery to bore out and thread the main through-bore and transverse bore, while the clutch-carrying bolt 36 enables simple but removable threaded connection of a conventional off-the-shelf fiber chuck to the block. It will be appreciated however that other embodiments may instead use a modified fiber chuck with its own external threading to make the removable threaded connection to the block, rather than relying on an axially bored bolt or other chuck-holding carrier to define the external male threads of this chuck-block connection. Connection of the fiber to the block in an air tight manner requires only passage of the fiber through the chuck, threading of the carrier bolt 36 to the block, and threading of the cap 48 to the chuck. Removal of the fiber 40, for example to swap the existing fiber for a replacement fiber of different length to vary the effective length of the gas cell, requires only the simple reversal of the installation process, i.e. loosening or removal of the cap 48, removal of the threaded carrier bolt 36 to allow withdrawal of the chuck of the block, and withdrawal of the fiber 40 from the chuck 38.

Figure 3A:
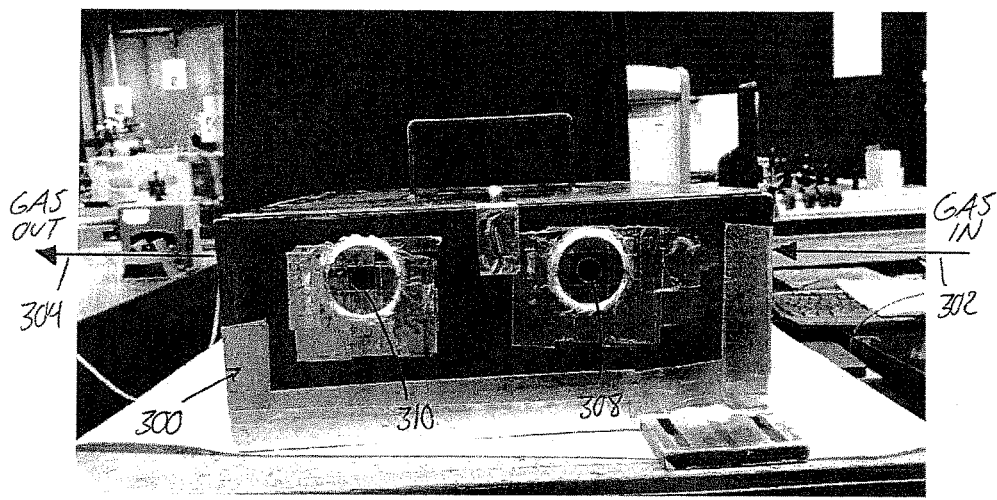
FIG. 3A is a photographic exterior view of a prototype of a second embodiment gas cell using a hollow-core PCF, where the entirety of the PCF resides inside a singular air-tight enclosure equipped with gas and optical inputs and outputs.

In addition to the first embodiment cell shown in FIG. 1, the present inventor also developed another gas cell (FIG. 3), which in its prototype form consist of a steel rectangular box 300 with a removable lid. A PCF 40 of desired length was placed inside the box. The steel box was fitted with a gas inlet 302 and a gas outlet 304 for introduction and evacuation of gas to the interior space of the box. An optical breadboard 306 was also placed inside the box on the floor thereof to make it possible to mount optical components inside the box. Light was coupled into (and out of) the PCF through the anti-reflection (AR) coated quartz windows 308, 310 installed in an exterior wall of the box (as shown in FIG. 3A). The fibers for ASE (or light) In/Out were mounted on three-axis translation stages with a combination of lenses, as described above for the first embodiment cell of FIG. 1 but omitted from FIG. 3 for illustrative simplicity.

While the illustrated embodiment features placement of the two quartz windows 308, 310 in the same wall of the box 300 to enable convenient mounting of the lens assemblies on a shared exterior breadboard at a singular side of the box, it will be appreciated that the windows could alternatively be installed in different walls of the box. The PCF 40 inside the box was mounted on fiber clamps 312, 314 [HFF003, Thorlabs] installed on the interior optical breadboard in close proximity to the quartz windows 308, 310 so as to hold the ends of the hollow-core PCF 40 in close relation to the windows to accept and return the ASE light from and to the exterior lens assemblies via said windows. The gas inlet fitting was mounted at one end of the box and connected to a supply of gas, and the gas outlet fitting was mounted at the opposing end of the box and connected to a vacuum pump. Initial gas in the steel box (e.g. ambient air, or remnant gas from a prior test) was first evacuated from one end of the box via the outlet 304, while maintaining the inlet closed via a control valve coupled thereto, and then the gas under investigation was allowed to enter from other end of the box via the input 302 by opening the control valve. It is also possible to evacuate and fill the PCF from both ends thereof since both ends of the PCF are open and reside inside the same air-tight enclosure.

In experimental use of the prototype, this process required a long time to fill and evacuate the PCF completely. To find the filling and evacuation time for a particular length of PCF, the output was monitored by observing absorption lines of 1% $C_2H_2$ in the C band region, where they are very strong. The disadvantage for this system was the long response time, which was due to the large volume of the gas cell compared to the volume of the PCF. The advantage of the gas cell is that one can drill holes along the length on the surface of PCF so that gas can diffuse faster inside the core of the fiber, and thus decrease the response time of the system [45,46].

While the prototype employed a steel box constructions, any box or container made of gas-impermeable solid material (e.g. aluminum, other metals) may similarly be used to form a singular enclosure whose interior space contains the entirety of hollow-core PCF, or at least the two ends thereof, and the pair of fiber clamps or other supports for supporting the ends of the hollow-core PCF in the appropriate positions optically aligned behind the quartz windows for optical communication therewith. A removable or openable and closeable lid is preferably employed to allow access to the hollow-core PCF for optional replacement thereof, for example to substitute a hollow-core PCF of one length for a replacement hollow-core PCF of a different length in order to easily change the effective length of the gas cell, provided that a suitable gasket or other sealing means is employed between the lid and the container walls when the lid is placed and secured in its closed position.

Below, Applicant presents experimental data based on the first embodiment gas cell of FIG. 1 for $N_2O$.

Figure 4:
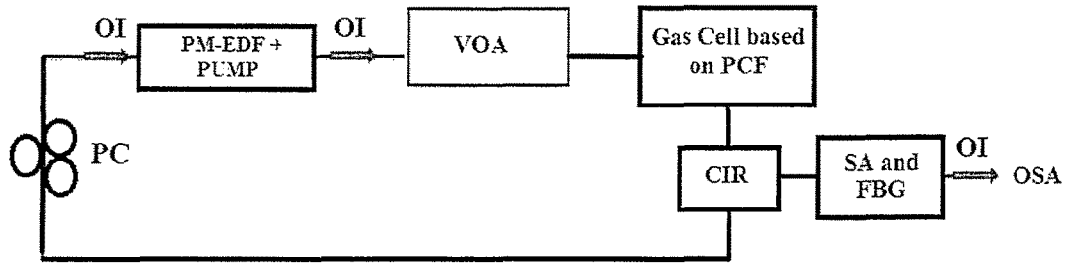
FIG. 4 is a schematic illustration of an experimental setup for the detection of trace gas. PUMP: pump laser; PM-EDF: Polarization-maintaining erbium-doped fiber; VOA: Variable optical attenuator; SA: Saturable absorber; FBG: Fiber Bragg grating; OSA: Optical spectrum analyzer; CIR: Polarization independent optical circulator; PC: Polarization controller and OI: Polarization independent optical isolator

FIG. 4 shows the schematic of the experimental setup used for the detection of $N_2O$. The first embodiment gas cell of FIG. 1 was used inside the cavity. The unidirectional resonant ring cavity consists of a polarization-maintaining erbium-doped fiber (PM-EDF); a variable optical attenuator (VOA) to adjust the loss in the cavity; an unpumped PM-EDF as the saturable absorber (SA); a fiber Bragg grating (FBG) of reflectivity 85.16%, peak wavelength ~1522.22 nm and bandwidth of 0.168 nm, where the peak wavelength of the FBG was close to P(12) rotational absorption line (FIG. 5A) of $N_2O$; and an all-fiber polarization controller to control the polarization state of the light inside the cavity. The detailed cavity design and advanced detection technique developed by the present inventors has been described in reference [6]. The presence of polarization-maintaining gain fiber and SA increases the stability of the laser wavelength.

The advantages of the detection system are: i) The laser generated by the system contains a multi-longitudinal mode, which increased the sensitivity of detection of gases at lower concentrations; ii) The system is capable of operating at room temperature (most of the currently commercially available systems require cooling below room temperature); iii) Standard optical components available from telecom industries were used for developing the device; iv) A gas cell based on hollow-core photonic crystal fiber makes the system compact and suitable for conversion into a hand held device; and v) The system can be used to detect various other gases (e.g. $NH_3$, $H_2S$ etc.) simply by changing the FBG.

Figure 5A:
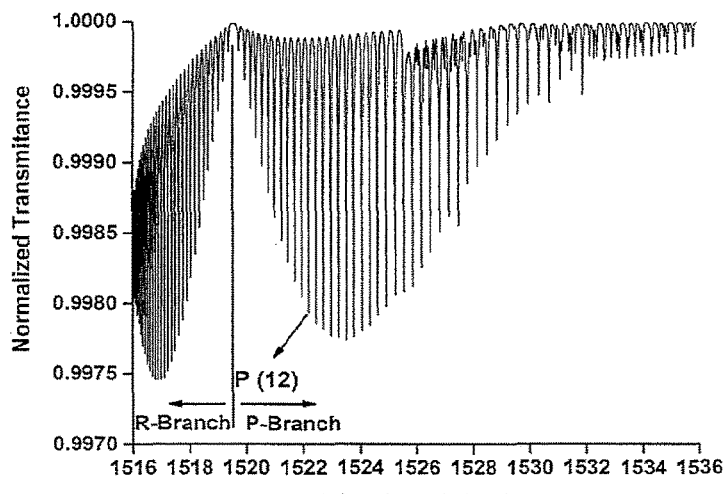
FIG. 5A shows theoretical rotational transition for $N_2O$ in the $3v_3$ band obtained using Spectral Calculator (GATS).

FIG. 5A shows the rotational lines in the $3u_3$ overtone band for $N_2O$, obtained using Spectral Calculator, GATS [10,20]. Although $N_2O$ possesses relatively strong absorption lines at ~1522 nm, the gain-coefficient of erbium-doped fiber is much lower compared to that in the C and L band regions. Further, erbium-doped fiber is a homogeneous gain medium at normal temperatures and the lasing wavelength is determined by the local maximum of the gain curve. For a ring cavity without a FBG lasing occurs in the C or L band.

Figure 3B:
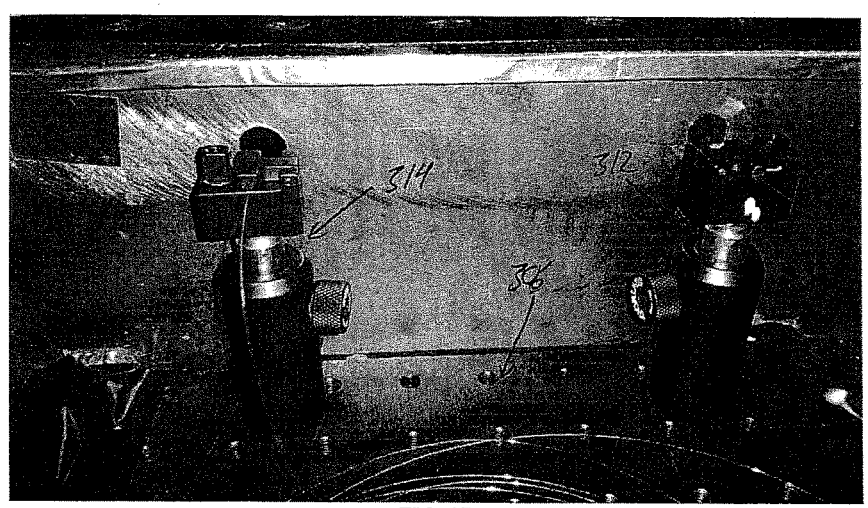
FIG. 3B is a photographic interior view of the second embodiment prototype of FIG. 3A with a lid of the enclosure removed for illustrative purpose.
Figure 5B:
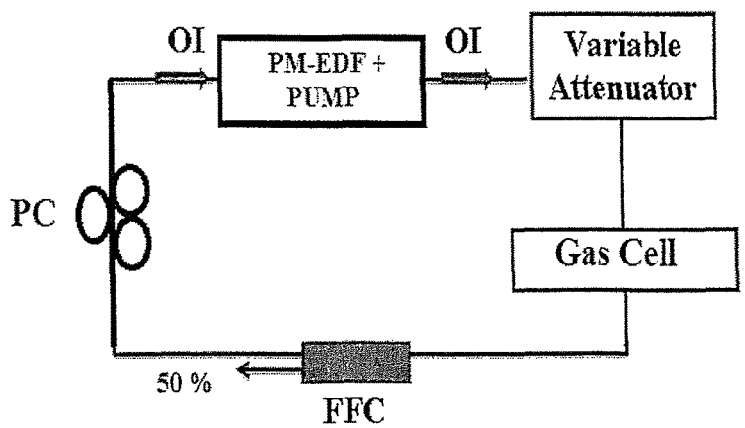
FIG. 5B schematically illustrates an experimental setup using the second embodiment gas cell to study intracavity laser absorption spectroscopy (ICAS) using amplified spontaneous emission (ASE) light inside the cavity.
Figure 6A:
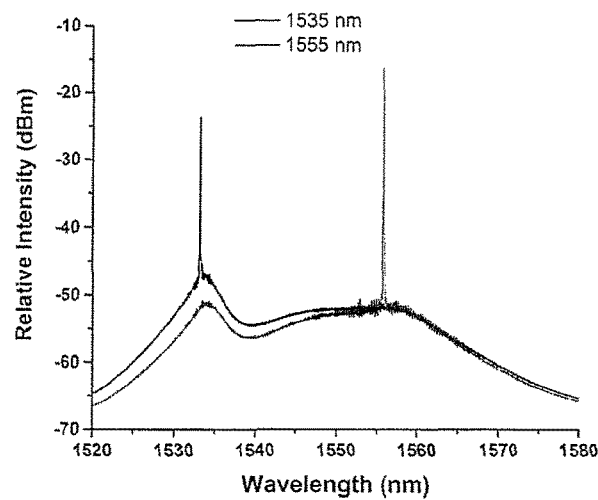
FIG. 6A shows output of the system obtained from the optical spectrum analyzer (OSA) of the FIG. 5 experimental setup as the variable optical attenuator (VOA) is adjusted.
Figure 6B:
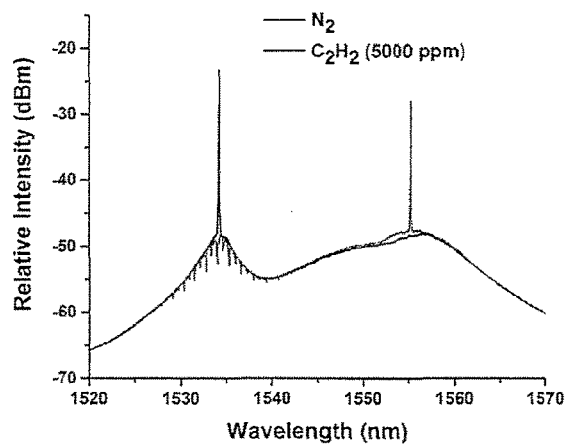
FIG. 6B shows output of the system obtained from the optical spectrum analyzer (OSA) of the FIG. 5 experimental setup using a hollow-core fiber (HC19-1550, NKT) of length 6 m as gas cell inside the cavity filled with 0.5% acetylene gas. The absorption lines are clearly visible in the C band.

FIG. 5B shows an ICLAS system developed using the second embodiment gas cell of FIG. 3, where the gas cell is coupled to a polarization controller (PC) by a fused fiber coupler (FFC). The cavity loss could be changed by adjusting the variable optical attenuator (VOA), which was adjusted to obtain an almost flat (60% inversion) spectrum in the C and L band regions. Once the system has reached this condition (called balanced condition), any small change in the cavity loss will switch the laser from the C band to the L band or vice versa. FIG. 6A shows the switching of the laser wavelength from the C band to the L band after a slight adjustment (i.e., increasing the loss in the C band region) of the VOA. In order to obtain very high sensitivity in detection using ASE inside the laser cavity, it is important to adjust the VOA (and thus the inversion level) in such a way that a very small change in attenuation can switch the laser between two bands when the laser operates under threshold conditions. A gas sample inside the ICLAS cavity also provide attenuation (due to absorption), which is similar to the VOA. FIG. 6B shows the switching of the laser line from the C band to the L band once the second embodiment gas cell of FIG. 3 was filled with 0.5% of $C_2H_2$. A few absorption lines are also visible in the C band, because the gas has many strong absorption lines in this region. The absorption coefficient for $N_2O$ is lower (~three orders of magnitude) than the $C_2H_2$ in the C band. Thus, it was not possible to take the advantage of ASE light available inside the cavity to detect $N_2O$ using the system as shown in FIG. 5B. The OSA (ANDO optical spectrum analyzer) spectra in the manuscript were collected using LABVIEW program (wavelength resolution: 0.005 nm and intensity resolution: 0.001 dBm) and each spectrum presented is the average of 10 scans.

Figure 7:
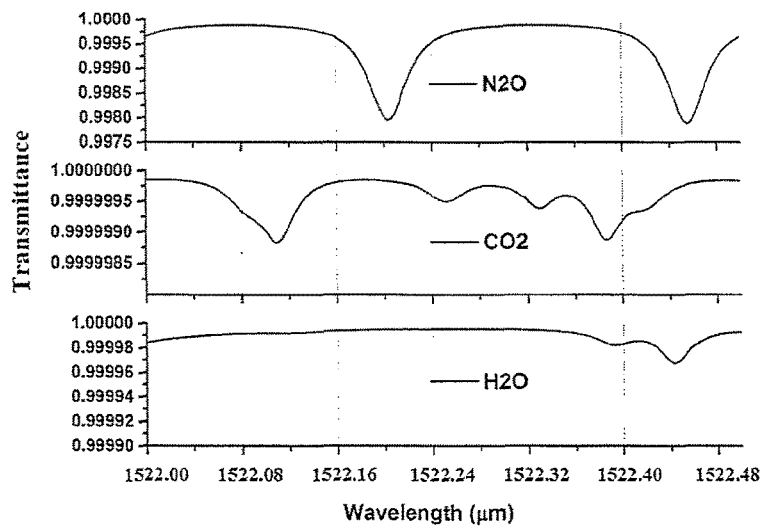
FIG. 7 shows theoretical absorption spectra obtained using Spectral Calculator (GATS).

The setup in FIG. 4 was developed in order to take the advantage of the ASE light inside the cavity in the ~1522 nm band, where $N_2O$ has high absorption compared to that in the C and L bands [6]. The FBG wavelength was chosen so that the peak wavelength is close to one of the absorption lines, P (12) rotation line in the $3v_3$ band [FIG. 5A], and does not interfere with the absorption lines due to the presence of $CO_2$ and $H_2O$ (FIG. 7). Two different lengths (20 m and 40 m) of PCF were used to make the gas cell, and the corresponding lengths of the unidirectional ring cavity were approximately 40 m and 60 m, respectively [including the length of the PCF]. The system produced a stable multi-longitudinal mode laser output at room temperature with a maximum separation of ~3 MHz for 40 m long PCF. A laser oscillating in multiple longitudinal modes is susceptible to mode hopping, but the small length of SA inside the cavity was able to eliminate the mode-hopping at normal room temperature [50,51]. Baev et al. reported properties of multi-longitudinal mode lasers and their application in ICLAS [52]. It was found that a multi-longitudinal mode laser provides very high sensitivity in ICLAS, if the homogeneously broadened gain bandwidth is larger than the absorption linewidth. In fact, the number of photons in a mode that matches the narrow band absorption line will decrease following the Beer-Lambert law. The ICAS produces a very good absorption spectrum if the absorption line of the gas sample is larger than the longitudinal mode separation [52]. In the present system, the absorption linewidth was larger than the separation between two longitudinal modes, so many longitudinal modes were superimposed within the absorption line. Further, Hansch et al. [53] also showed an increase of absorption sensitivity by a factor of $10^5$ due to the presence of a number of oscillating modes.

The experimental setup described in FIG. 4 produced a multi-longitudinal mode laser wavelength, which was selected by the FBG. The laser was kept under the threshold condition, so that the wavelengths related to the ASE light close to the laser wavelength were also close to the threshold condition. Thus, the photons corresponding to ASE light inside the cavity circulated multiple times and enhanced the effective path length of the cavity. In turn, the sensitivity of detection was also enhanced due to the large absorption path length.

Figure 8B:
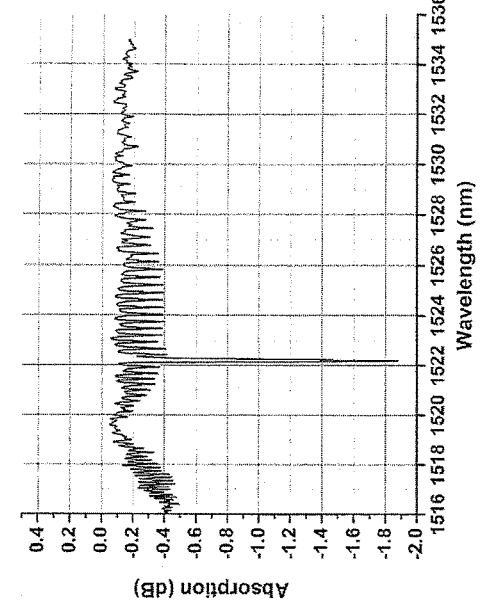
FIG. 8B shows direct absorption spectra of $N_2O$ gas after subtracting the $N_2$ gas spectrum as background for a 20 meter length of PCF in the first embodiment gas cell.
Figure 8A:
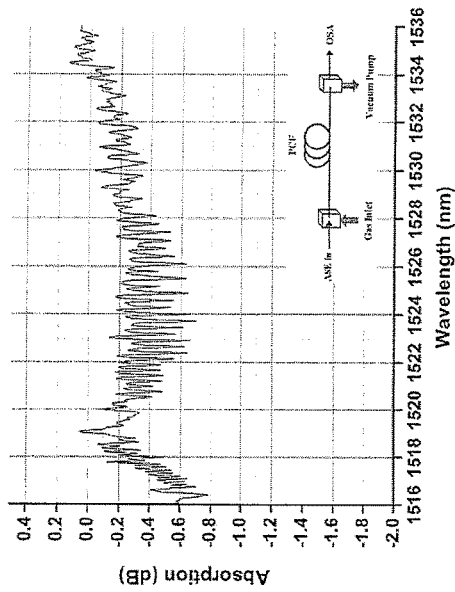
FIG. 8A shows direct absorption spectra of $N_2O$ gas after subtracting the $N_2$ gas spectrum as background for a 40 meter length of PCF in the first embodiment gas cell.

FIG. 8 shows the absorption spectra from the direct absorption of the 10% $N_2O$ (Praxair, Canada, certified concentration of $N_2O$: 10%+$N_2$ balance) gas using a 40 m and 20-meter long PCF after subtracting the reference gas $N_2$, obtained using the first embodiment gas cell shown in FIG. 1. The gas was allowed to diffuse through one end and the other end was maintained at constant vacuum level. The ASE from the PM-EDF [$I_P$=75 mA] was used as the input light for the direct absorption spectroscopic (DAS) measurement [Note: The laser cavity was not closed]. The output obtained was monitored using the OSA. The absorption lines of the gas disappeared after a few cycles of evacuation and filling with $N_2$. The hollow-core (20 micron diameter) of the PCF was surrounded by small, micron-order holes. The longer evacuation time was due to the presence of these gas-filled smaller holes. It is anticipated that most of the laser power is confined to the core and the effect of absorption due to gas inside the surrounding small holes is minimal or not significant. It is also possible to obtain the DAS spectrum by using a tunable laser.

Figure 9B:
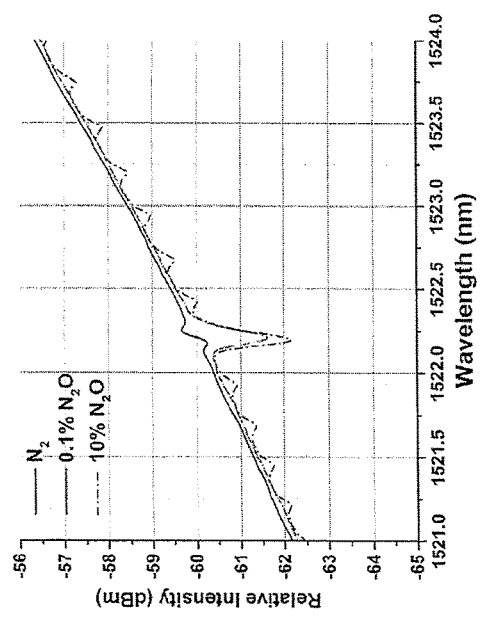
FIG. 9B shows absorption spectrum of 10% $N_2O$ from the FIG. 4 experimental setup after subtracting the $N_2$ gas spectrum as background, for a 40 meter length of PCF in the first embodiment gas cell.
Figure 9A:
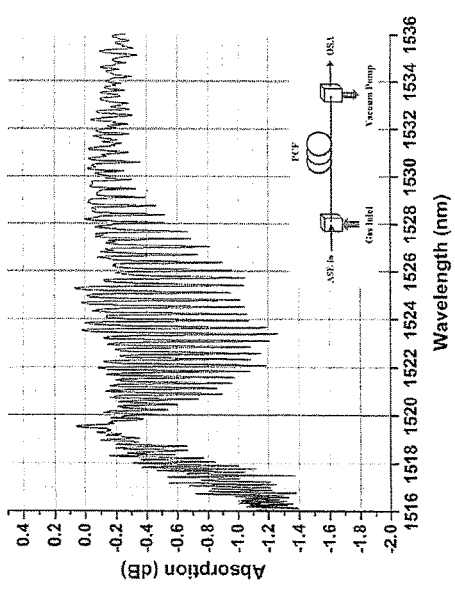
FIG. 9A shows absorption spectra of $N_2O$ gas from the FIG. 4 experimental setup at two different concentrations.
Figure 10A:
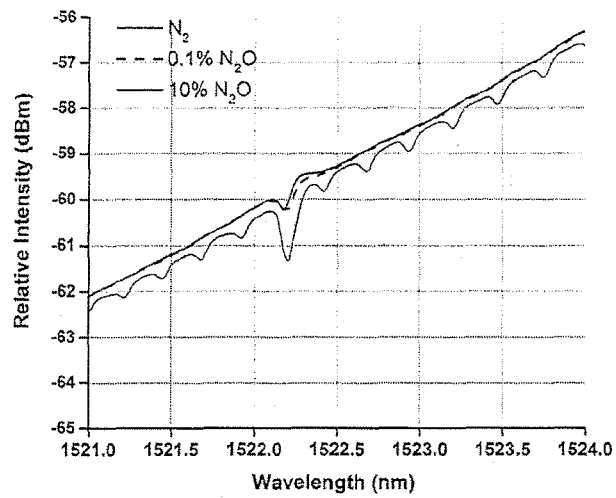
FIG. 10A shows absorption spectra of N2O gas from the FIG. 4 experimental setup at two different concentrations.
Figure 10B:
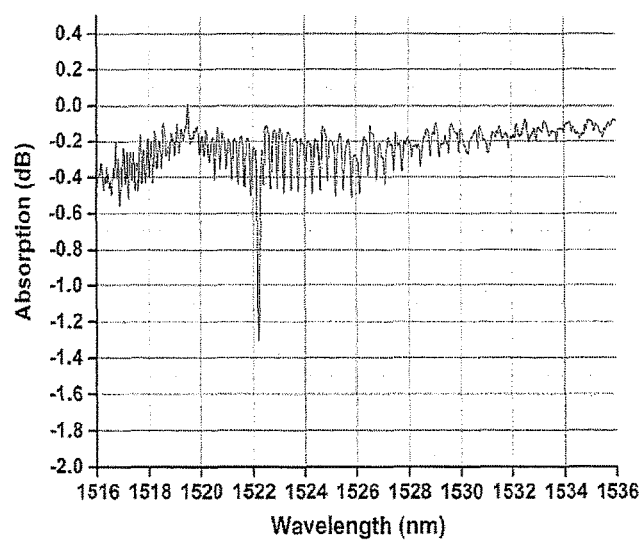

FIG. 9A shows the transmission spectra of the experimental setup described in FIG. 4 with the reference gas $N_2$ (Praxair, Canada, Research Grade, Nitrogen 6.0) and $N_2O$ (Praxair, Canada, certified concentration of $N_2O$: 10% +$N_2$ balance and 0.1%+$N_2$ balance) with 40 m PCF for the gas cell. The absorption spectrum in FIG. 9B was obtained by subtracting the spectra for $N_2O$ (10%) and $N_2$ shown in FIG. 9A. The system described in FIG. 4 was operating under threshold condition ($I_p$=147.5 mA). It is to be noted that that the gas cell was flushed with $N_2$ before and after the scanning with $N_2O$ gas. The experiment was repeated with 20 m long PCF. FIG. 10 shows output spectra obtained using a 20 m long PCF as the gas cell inside the system in FIG. 4, for 10% and 0.1% $N_2O$, respectively.

Figure 11:
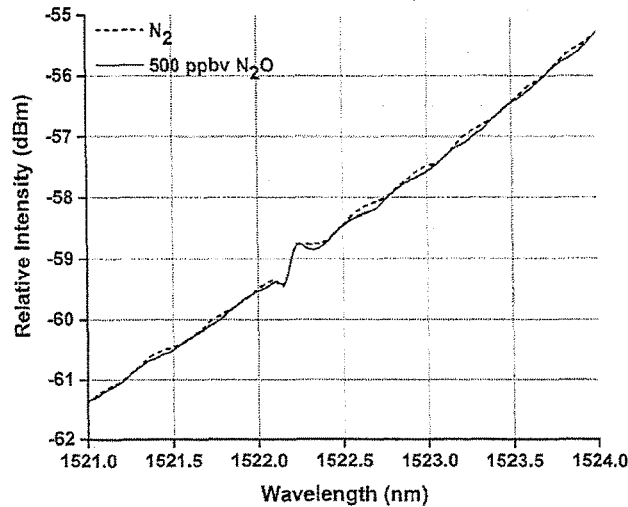
FIG. 11 shows absorption spectrum of 500 ppbv $N_2O$ gas for a 40 meter length of PCF in the first embodiment gas cell.

It is clear from the spectra in FIG. 8, obtained using DAS, and in FIGS. 9 and 10, using ICLAS, that the specificity and sensitivity of detection increases at the FBG location. Further, the application of a FBG eliminates any overlap with absorption lines due to other gases in the mixture. In the present case, the inventor used the absorption line corresponding to the P (12) line of $N_2O$. The experiments were performed with lower concentrations of $N_2O$ gas. The minimum concentration the system can detect with 40 m long PCF after a longer evacuation and filling time (~4 hours) was ~500 ppbv (FIG. 11; Praxair, Canada, certified concentration of $N_2O$: 520 ppbv+$N_2$ balance).

In summary, presented herein are two gas cells based on hollow-core photonic crystal fiber for the detection of nitrous oxide gas. In prototype experimentation, the gas cell was incorporated inside a laser cavity as an intracavity gas cell. At present, the evacuation and filling time for the gas through the PCF may be too long for use where fast response is important. The sensitivity of the system can be increased by improving the responsivity or by reducing gas evacuation and filling times. In addition, the laser cavity supported multi-longitudinal modes, which increased the sensitivity further. The system is capable of operating at room temperature and over a wide set of wavelengths. One can select the gas absorption line of any trace gas by using a tunable FBG. The system can be used as a hand-held device.

REFERENCES

1. F. A. Phillips, R. Leuning, R. Baigenta, K. B. Kelly, and O. T. Denmead, Agricultural and Forest Meteorology 143, 92 (2007).
2. A. J. Glenn, M. Tenuta, B. D. Amiro, S. E. Maas, and C. Wagner-Riddle, Agricultural and Forest Meteorology 166, 41 (2012).
3. G. Whitenett, G. Stewart, H. B. Yu, and B. N. Culshaw, Journal of Lightwave Technology 22, 813 (2004).
4. N. Arsad, M. Li, G. Stewart, and W. Johnstone, Journal of Lightwave Technology 29, 782 (2011).
5. G. Stewart, P. Shields, and B. Culshaw, Measurement Science & Technology 15, 1621 (2004).
6. J. K. Valiunas, G. Stewart, and G. Das, Ieee Photonics Technology Letters 28, 359 (2016).
7. Plyler E. K., Tidwell E. D., and Maki A. G., Journal of Research of the National Bureau of Standards—A. Physics and Chemistry 68A, 79 (1963).
8. A. Campargue, D. Permogorov, M. Bach, M. A. Temsamani, J. V. Auwera, M. Herman, and M. Fujii, Journal of Chemical Physics 103, 5931 (1995).
9. F. G. Wienhold, H. Fischer, and G. W. Harris, Infrared Physics and Technology 37, 67 (1996).
10. R. A. Toth, Journal of Molecular Spectroscopy 197, 158 (1999).
11. G. Weirauch, A. A. Kachanov, A. Campargue, M. Bach, M. Herman, and J. Vander Auwera, Journal of Molecular Spectroscopy 202, 98 (2000).
12. A. M. Parkes, A. R. Linsley, and A. J. Orr-Ewing, Chemical Physics Letters 377, 439 (2003).
13. E. Bertseva, A. Campargue, V. I. Perevalov, and S. A. Tashkun, Journal of Molecular Spectroscopy 226, 196 (2004).
14. L. Wang, V. I. Perevalov, S. A. Tashkun, B. Gao, L. Y. Hao, and S. M. Hu, Journal of Molecular Spectroscopy 237, 129 (2006).
15. A. W. Liu, S. Kassi, P. Malara, D. Romanini, V. I. Perevalov, S. A. Tashkun, S. M. Hu, and A. Campargue, Journal of Molecular Spectroscopy 244, 33 (2007).
16. A. W. Liu, S. Kassi, V. I. Perevalov, S. A. Tashkun, and A. Campargue, Journal of Molecular Spectroscopy 244, 48 (2007).
17. H. Y. Ni, K. F. Song, V. I. Perevalov, S. A. Tashkun, A. W. Liu, L. Wang, and S. M. Hu, Journal of Molecular Spectroscopy 248, 41 (2008).
18. K. F. Song, A. W. Liu, H. Y. Ni, and S. M. Hu, Journal of Molecular Spectroscopy 255, 24 (2009).
19. B. Gao, C. Y. Wang, Y. Lu, A. W. Liu, and S. M. Hu, Journal of Molecular Spectroscopy 259, 20 (2010).

20. L. S. Rothman, I. E. Gordon, Y. Babikov, A. Barbe, D. C. Benner, P. F. Bernath, M. Birk, L. Bizzocchi, V. Boudon, L. R. Brown, A. Campargue, K. Chance, E. A. Cohen, L. H. Coudert, V. M. Devi, B. J. Drouin, A. Fayt, J. M. Flaud, R. R. Gamache, J. J. Harrison, J. M. Hartmann, C. Hill, J. T. Hodges, D. Jacquemart, A. Jolly, J. Lamouroux, R. J. Le Roy, G. Li, D. A. Long, O. M. Lyulin, C. J. Mackie, S. T. Massie, S. Mikhailenko, H. S. P. Muller, O. V. Naumenko, A. V. Nikitin, J. Orphal, V. Perevalov, A. Perrin, E. R. Polovtseva, C. Richard, M. A. H. Smith, E. Starikova, K. Sung, S. Tashkun, J. Tennyson, G. C. Toon, V. G. Tyuterev, and G. Wagner, Journal of Quantitative Spectroscopy & Radiative Transfer 130, 4 (2013).
21. A. Lancia, Optical Sensors and Microsystems: New Concepts, Materials, Technologies 235 (2000).
22. T. Ritari, H. Ludvigsen, and J. C. Petersen, Spectroscopy 20, 30-+(2005).
23. J. P. Parry, B. C. Griffiths, N. Gayraud, E. D. McNaghten, A. M. Parkes, W. N. MacPherson, and D. P. Hand, Measurement Science & Technology 20, (2009).
24. J. C. Knight, J. Broeng, T. A. Birks, and P. St. J. Russell, Science 282, 1476 (1998).
25. F. Benabid and P. St. J. Russell, Proceedings of SPIE: Photonic Crystal Materials and Devices III 5733, 176 (2005).
26. M. N. Petrovich, F. Poletti, and D. J. Richardson, (IEEE, 2009).
27. M. N. Petrovich, A. van Brakel, F. Poletti, K. Mukasa, E. Austin, V. Finazzi, P. Petropoulos, E. O'Driscoll, M. Watson, T. DelMonte, J. P. Dakin, and D. J. Richardson, Proceedings of SPIE: Photonic Crystals and Photonic Crystal Fibers for Sensing Applications 6005, 78 (2005).
28. T. Ritari, J. Tuominen, H. Ludvigsen, J. C. Petersen, T. Sorensen, T. P. Hansen, and H. R. Simonsen, Optics Express 12, 4080 (2004).
29. A. Duval, M. Lhoutellier, J. B. Jensen, P. E. Hoiby, V. Missier, L. H. Pedersen, T. P. Hansen, A. Bjarklev, and O. Bang, Proceedings of IEEE: Sensors 3, 1222 (2004).
30. F. Benabid, F. Couny, J. C. Knight, T. A. Birks, and P. S. Russell, Nature 434, 488 (2005).
31. A. van Brakel, C. Jauregui, T. T. Ng, P. Petropoulos, J. P. Dakin, C. Grivas, M. N. Petrovich, and D. J. Richardson, (IEEE, 2008).
32. D. Munzke, M. Bohm, and O. Reich, Journal of Lightwave Technology 33, 2524 (2015).
33. F. Magaelhaes, J. P. Carvalho, L. A. Ferreira, F. M. Araujo, and J. L. Santos, 2008), pp. 1277.
34. H. W. Zhang, Y. Lu, L. C. Duan, Z. Q. Zhao, W. Shi, and J. Q. Yao, Optics Express 22, 24545 (2014).
35. D. S. Bomse and M. N. Ediger, 2014).
36. A. M. Cubillas, J. M. Lazaro, O. M. Conde, M. N. Petrovich, and J. M. Lopez-Higuera, Sensors 9, 6261 (2009).
37. A. M. Cubillas, J. Hald, and J. C. Petersen, Optics Express 16, 3976 (2008).
38. C. Y. Tao, H. M. Wei, and W. L. Feng, Optics Express 24, 2806 (2016).
39. X. F. Li, J. X. Liang, S. Lin, Y. Zimin, Y. P. Zhang, and T. Ueda, IEEE Sensors Journal 12, 2362 (2012).
40. J. Henningsen and J. Hald, Applied Optics 47, 2790 (2008).
41. I. Dicaire, J. C. Beugnot, and L. Thevenaz, Applied Optics 49, 4604 (2010).
42. Y. L. Hoo, W. Jin, H. L. Ho, J. Ju, and D. N. Wang, Sensors and Actuators B-Chemical 105, 183 (2005).
43. I. Dicaire, J. C. Beugnot, and L. Thevenaz, 2010), pp. 76530L.
44. M. Amanzadeh, E. Sheridan, S. M. Aminossadati, M. S. Kizil, and W. P. Bowen, 2013).
45. C. J. Hensley, D. H. Broaddus, C. B. Schaffer, and A. L. Gaeta, Optics Express 15, 6690 (2007).
46. A. van Brakel, C. Grivas, M. N. Petrovich, and D. J. Richardson, Optics Express 15, 8731 (2007).
47. R. Dhawan, M. M. Khan, N. Panwar, U. Tiwari, R. Bhatnagar, and S. C. Jain, Optik 124, 3671 (2013).
48. J. M. Lazaro, A. M. Cubillas, M. Silva-Lopez, O. M. Conde, M. N. Petrovich, and J. M. Lopez-Higuera, 2008).
49. S. H. Kassani, J. Park, Y. Jung, J. Kobelke, and K. Oh, Optics Express 21, 14074 (2013).
50. Valiunas J. K. and das G. Tunable Single-Longitudinal-Mode High-Power Fiber Laser. International Journal of Optics 2012, 1-6. 2012. Ref Type: Generic
51. P. J. Moore, Z. J. Chaboyer, and G. Das, Optical Fiber Technology 15, 377 (2009).
52. V. M. Baev, Latz T., and Toschek P. E., Applied Physics B 69, 171 (1999).
53. T. Hansch, A. L. Schawlow, and P. Toschek, Quantum Electronics, IEEE Journal of 8, 802 (1972).

Since various modifications can be made in the present invention as herein above described, and many apparently widely different embodiments of same made, it is intended that all matter contained in the accompanying specification shall be interpreted as illustrative only and not in a limiting sense.

The invention claimed is:

1. A gas absorption cell apparatus comprising at least one terminal block for coupling to a first end of a hollow core photonic crystal fiber to cooperate with a like terminal block at an opposing second end of the hollow core photonic crystal fiber to form a fiber-based gas absorption cell, wherein each terminal block comprises:
   a solid block of air-impermeable material having a main through-bore extending fully through the block from an optical-coupling end of said block and opposing fiber-coupling end of said block;
   an optical window fitted in the main through-bore at the optical-coupling end of said block to enable admission or exit of light energy to or from said main through-bore;
   an optical fiber chuck fitted in the main through-bore at the fiber-coupling end of said block to receive a respective end of the hollow core photonic crystal fiber and position said end within the main through-bore in alignment behind said optical window for optical communication therewith;
   a transverse bore extending into said block from a gas-coupling side thereof and intersecting with said main through-bore at an intermediate location between said ends of the block to enable admission or evacuation of gas to or from the end of the hollow core photonic crystal fiber via said transverse bore; and
   external threading carried on the fiber chuck and internal threads provided in the main through-bore adjacent the fiber-coupling end of the block, the fiber chuck being fitted with the main through-bore by engagement of the external threading on the fiber chuck with the internal threads of the main through-bore;
   wherein the external threading carried on the fiber chuck is defined by an externally threaded carrier through which the fiber chuck axially extends.

2. The apparatus of claim 1 comprising internal threading within the transverse bore for receiving a threaded gas fitting at the gas-coupling side of the block end for said admission or evacuation of said gas via said fitting.

3. The apparatus of claim 1 wherein the main through-bore, at the optical-coupling end thereof, comprises a counter-bored area of enlarged diameter in which the optical window is mounted.

4. A gas absorption cell apparatus comprising at least one terminal block for coupling to a first end of a hollow core photonic crystal fiber to cooperate with a like terminal block at an opposing second end of the hollow core photonic crystal fiber to form a fiber-based gas absorption cell, wherein each terminal block comprises:
a solid block of air-impermeable material having a main through-bore extending fully through the block from an optical-coupling end of said block and opposing fiber-coupling end of said block;
an optical window fitted in the main through-bore at the optical-coupling end of said block to enable admission or exit of light energy to or from said main through-bore;
an optical fiber chuck fitted in the main through-bore at the fiber-coupling end of said block to receive a respective end of the hollow core photonic crystal fiber and position said end within the main through-bore in alignment behind said optical window for optical communication therewith; and
a transverse bore extending into said block from a gas-coupling side thereof and intersecting with said main through-bore at an intermediate location between said ends of the block to enable admission or evacuation of gas to or from the end of the hollow core photonic crystal fiber via said transverse bore;
wherein the fiber chuck has an externally threaded end disposed outside the block, a cap with a threaded axial bore extending thereinto from a first end of the cap is engaged to the externally threaded end of the fiber chuck via mating of said threaded axial bore with the threaded end of the fiber chuck, a seal is axially compressed between an end of the axial bore and the threaded end of the fiber chuck and is circumferentially tightened around the fiber, which passes through the threaded bore of the cap via a smaller axial bore that communicates therewith.

5. The apparatus of claim 1 wherein the externally threaded-carrier comprises an externally threaded shaft and an enlarged head of greater diameter than said threaded shaft by which rotation of the externally threaded carrier can be driven to engage and disengage said externally threaded carrier from the internal threading of the main through-bore.

6. The apparatus of claim 1 comprising an o-ring seal circumferentially disposed around the fiber chuck and clamped between an end of the externally threaded carried carrier and an inwardly reaching shoulder of the block at a transition between a counter-bored section thereof at which the internal threads are defined and an adjacent reduced-diameter section of the main-through bore.

7. The apparatus of claim 4 comprising a threaded connection between the fiber chuck and the block, whereby the fiber chuck is readily removable from the block for selective disconnection of the respective end of the hollow core photonic crystal fiber.

8. The apparatus of claim 1 wherein the fiber chuck has an externally threaded end disposed outside the block past the externally threaded carrier, a cap with a threaded axial bore extending thereinto from a first end of the cap is engaged to the externally threaded end of the fiber chuck via mating of said threaded axial bore with the threaded end of the fiber chuck, and a seal is axially compressed between an end of the axial bore and the threaded end of the fiber chuck and is circumferentially tightened around the fiber, which passes through the threaded bore via a smaller inlet bore that communicates therewith.

9. The apparatus of claim 1 wherein said at least one terminal block comprises two identical terminal blocks.

10. The apparatus of claim 4 wherein said at least one terminal block comprises two identical terminal blocks.

11. A method of producing a gas absorption cell apparatus comprising at least one terminal block for coupling to a first end of a hollow core photonic crystal fiber to cooperate with a like terminal block at an opposing second end of the hollow core photonic crystal fiber to form a fiber-based gas absorption cell, wherein:
each terminal block comprises:
a solid block of air-impermeable material having a main through-bore extending fully through the block from an optical-coupling end of said block and opposing fiber-coupling end of said block;
an optical window fitted in the main through-bore at the optical-coupling end of said block to enable admission or exit of light energy to or from said main through-bore;
an optical fiber chuck fitted in the main through-bore at the fiber-coupling end of said block to receive a respective end of the hollow core photonic crystal fiber and position said end within the main through-bore in alignment behind said optical window for optical communication therewith; and
a transverse bore extending into said block from a gas-coupling side thereof and intersecting with said main through-bore at an intermediate location between said ends of the block to enable admission or evacuation of gas to or from the end of the hollow core photonic crystal fiber via said transverse bore; and
said method comprises, for each terminal block of said apparatus, obtaining a solid block of air-impermeable material, boring the main through-bore through said solid block from a first end thereof to an opposing second end, boring the transverse bore into said solid block from one side thereof to a point intersecting said main through-bore at an intermediate location between said first and second ends of the solid block, mounting the optical window in the main through-bore at the first end of the solid block, and providing a releasable connection to the main through-bore at the second end of the block for removable mounting of the fiber chuck in the main through-bore in order to hold the respective end of the hollow core photonic crystal fiber within the main through-bore at a position behind the optical window and in fluid communication with the transverse bore to enable optical communication between said optical window and said end of the hollow core photonic crystal fiber and admission or evacuation of gas to or from the hollow core photonic crystal fiber via said transverse bore.

12. The method of claim 11 comprising counter-boring the main through-bore at the first end of the block to form an area of enlarged diameter for mounting of the optical window.

13. The method of claim 12 comprising introducing a flowable sealant into said area of enlarged diameter during installation of the optical window therein to create an air-tight seal between the optical window and the main through-bore that prevents escape of gas from the main through-bore at the first end of the block.

14. The method of claim 11 comprising boring the main through-bore with multiple diameters, including boring a reduced diameter section of the main through-bore at an intermediate location between the second end of the block and the location at which the transverse bore intersects the main through-bore, and boring a larger counter-bored section of the main through-bore at the second end of the block so that a transition between the reduced diameter section and the larger counter-bored section defines an inwardly reaching shoulder for receiving an o-ring that is compressed against said shoulder by threaded coupling of the fiber chuck to the block at the second end thereof.

15. The method of claim 11 comprising coupling the fiber chuck to the block in a position placing an externally threaded end of the chuck outside the block and supporting the hollow core photonic crystal fiber in a position passing axially through said chuck, threading a removable cap, through which the hollow core photonic crystal fiber passes, onto the externally threaded end of the fiber chuck, and advancing said cap into a tightened position axially compressing a seal against the threaded end of the fiber chuck and circumferentially tightening said seal around the hollow core photonic crystal fiber.

16. A method of adjusting the effective length of a gas absorption cell apparatus comprising two terminal blocks for coupling to respective ends of a hollow core photonic crystal fiber to form a fiber-based gas absorption cell, wherein:
    each terminal block comprises
        a solid block of air-impermeable material having a main through-bore extending fully through the block from an optical-coupling end of said block and opposing fiber-coupling end of said block;
        an optical window fitted in the main through-bore at the optical-coupling end of said block to enable admission or exit of light energy to or from said main through-bore;
        an optical fiber chuck fitted in the main through-bore at the fiber-coupling end of said block to receive a respective end of the hollow core photonic crystal fiber and position said end within the main through-bore in alignment behind said optical window for optical communication therewith; and
        a transverse bore extending into said block from a gas-coupling side thereof and intersecting with said main through-bore at an intermediate location between said ends of the block to enable admission or evacuation of gas to or from the end of the hollow core photonic crystal fiber via said transverse bore; and
    said method comprises with the apparatus in an initial state in which an initial hollow core photonic crystal fiber runs between the two terminal blocks with opposing ends of said hollow core photonic crystal fiber respectively held in the main through-bore of the terminals blocks behind the optical windows thereof, decoupling said opposing ends of said initial hollow core photonic crystal fiber from said terminal blocks, and substituting a replacement hollow core photonic crystal fiber of different length by respectively coupling opposing ends of the replacement hollow core photonic crystal fiber to said terminal blocks in place of the initial hollow core photonic crystal fiber.

17. A hollow core photonic crystal fiber gas absorption cell apparatus comprising a singular enclosure that comprises a plurality of exterior walls delimiting a singular interior space that is closed or closable in an air-tight manner sealed off from a surrounding exterior environment by said exterior walls; optical input and output windows bath installed on one or more of said exterior walls surrounding the same singular interior space and both optically communicating the same singular interior space of the singular enclosure with the surrounding exterior environment; first and second fiber supports both mounted within the same singular interior space of the singular enclosure, the first fiber support residing at a first location proximate the optical input window to support a first end of a hollow core photonic crystal fiber inside the singular interior space at said first location proximate said optical input window to accept incoming light energy admitted to the singular interior space of the singular enclosure via said optical input window, and the second fiber support residing at a second location proximate the optical output window to support a second end of the hollow core photonic crystal fiber inside the singular interior space at said second location proximate said optical output window to release light energy from said hollow core photonic crystal fiber to the exterior environment via said optical output window; a gas inlet located on one of the exterior walls surrounding said same singular interior space, said gas inlet fluidly communicating with said same singular interior space and being connected or connectable to a supply of gas to admit gas into said same singular interior space; and a gas outlet located on one of the exterior walls surrounding said same singular interior space, said gas outlet also fluidly communicating with the same singular interior space for evacuating said gas from said same singular interior space, whereby said gas admitted into said same singular interior space is admissible and evacuatable to and from the hollow core photonic crystal fiber via the ends of said hollow core photonic crystal fiber positioned inside said same singular interior space by said fiber supports.

18. A hollow core photonic crystal fiber gas absorption cell apparatus comprising a singular enclosure that comprises a plurality of exterior walls delimiting a singular interior space that is closed or closable in an air-tight manner sealed off from a surrounding exterior environment by said exterior walls; optical input and output windows installed on one or more of said exterior walls surrounding the same singular interior space and both optically communicating the same singular interior space of the singular enclosure with the surrounding exterior environment; a hollow core photonic crystal fiber situated entirely within the same singular interior space of the singular enclosure with a first end of the hollow core photonic crystal fiber situated inside said same singular interior space at a first location proximate said optical input window to accept incoming light energy admitted to the same singular interior space of the enclosure via said optical input window, and a second end of the hollow core photonic crystal fiber situated inside said same singular interior space at a second location proximate said optical output window to release outgoing light energy from said the hollow core photonic crystal fiber to the exterior environment via said optical output window; a gas inlet located on one of the exterior walls surrounding said same singular interior space, said gas inlet fluidly communicating with said same singular interior space and connected or connectable to a supply of gas to admit gas into said same singular interior space and a gas outlet located on one of the exterior walls surrounding said same singular interior space, said gas outlet also fluidly communicating with the same singular interior space for evacuating said gas from said interior space, whereby said gas admitted into said interior space is admissible and evacuatable to and from the hollow core photonic crystal fiber via the ends of said hollow core photonic crystal fiber positioned inside said same singular interior space.

19. The apparatus of 17 wherein a surface of the hollow core photonic crystal fiber is provided with holes at intermediate locations between the ends of the hollow core photonic crystal fiber.

20. The apparatus of 18 wherein a surface of the hollow core photonic crystal fiber is provided with holes at intermediate locations between the ends of the hollow core photonic crystal fiber.

* * * * *